(12) United States Patent
Renard et al.

(10) Patent No.: US 9,456,848 B2
(45) Date of Patent: Oct. 4, 2016

(54) EXTERNAL FIXATORS

(71) Applicant: Xavier Renard, Vauhallan (FR)

(72) Inventors: Xavier Renard, Vauhallan (FR);
Philippe Pelissier, Merignac (FR)

(73) Assignee: Xavier Renard, Vauhallan (FR)

( * ) Notice: Subject to any disclaimer, the term of this patent is extended or adjusted under 35 U.S.C. 154(b) by 0 days.

(21) Appl. No.: 14/785,721

(22) PCT Filed: Mar. 24, 2014

(86) PCT No.: PCT/FR2014/000061
§ 371 (c)(1),
(2) Date: Oct. 20, 2015

(87) PCT Pub. No.: WO2014/177775
PCT Pub. Date: Nov. 6, 2014

(65) Prior Publication Data
US 2016/0066955 A1 Mar. 10, 2016

(30) Foreign Application Priority Data

Apr. 30, 2013 (FR) .................................. 13 00999

(51) Int. Cl.
*A61B 17/00* (2006.01)
*A61B 17/60* (2006.01)
(Continued)

(52) U.S. Cl.
CPC ........... *A61B 17/60* (2013.01); *A61B 17/6491* (2013.01); *A61B 17/66* (2013.01); *A61B 2017/606* (2013.01)

(58) Field of Classification Search
CPC ...... A61B 17/58; A61B 17/60; A61B 17/66; A61B 17/6491; A61B 2017/606

USPC ........................................................... 606/54
See application file for complete search history.

(56) References Cited

U.S. PATENT DOCUMENTS 3,511,280 A * 5/1970 Mercier .................... F15B 1/20
138/30
3,807,394 A * 4/1974 Attenborough .... A61B 17/7225
606/60

(Continued)

FOREIGN PATENT DOCUMENTS

EP   1 898 815 B2   3/2008
FR   2 886 129 A1   12/2006

OTHER PUBLICATIONS

International Search Report, dated Jul. 4, 2014, from corresponding PCT application.

*Primary Examiner* — Ellen C Hammond
*Assistant Examiner* — Stuart S Bray
(74) *Attorney, Agent, or Firm* — Young & Thompson

(57) ABSTRACT

A resilient external fixator between first and second bone portions includes a spring 11 of axis 12, a body 14, elements 15 for mounting the body to co-operate with the spring, a pin 16 fastened to the first bone and passing through the spring, a second body 22 including a base 122 and a projecting portion 44 that is secured to the base, one end 47 of the helical spring being mounted in co-operation about the projecting portion, and elements 24 for connecting the body with the bone portion $O_2$ and the helical spring. The projecting portion presents a section that increases in continuous manner from its free end 48 until it reaches its end 46, the end 47 of the spring having an inside section that is greater than the section of the free end 48 and less than the cross-section of the end 46.

14 Claims, 1 Drawing Sheet

Figure 1:
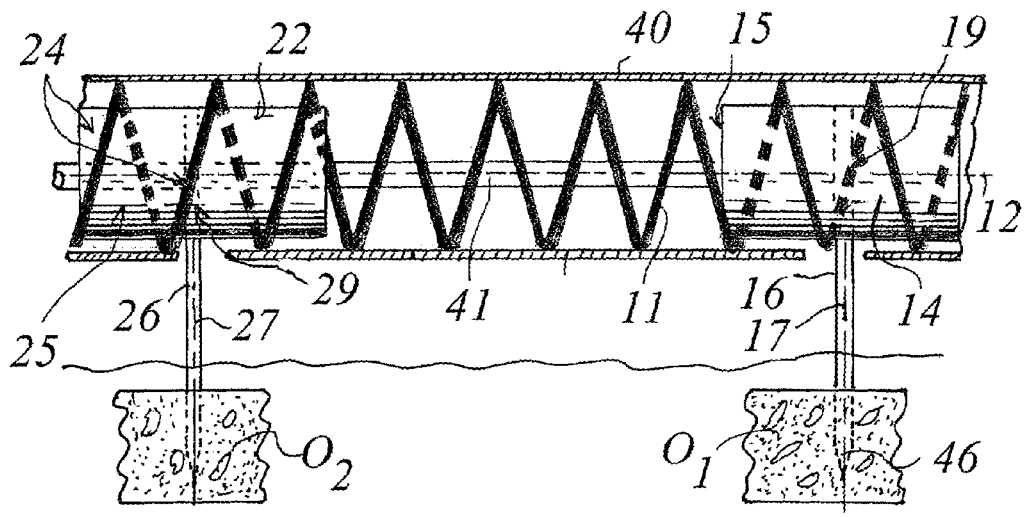

(51) Int. Cl.
*A61B 17/64* (2006.01)
*A61B 17/66* (2006.01)

(56) References Cited

U.S. PATENT DOCUMENTS

| | | | | | |
|---|---|---|---|---|---|
| 4,502,473 | A | * | 3/1985 | Harris | A61B 17/6491 606/58 |
| 5,347,894 | A | * | 9/1994 | Fischer | A61B 17/6433 606/104 |
| 5,375,823 | A | * | 12/1994 | Navas | A61B 17/7005 267/153 |
| 5,540,688 | A | * | 7/1996 | Navas | A61B 17/7005 606/266 |
| 5,672,175 | A | * | 9/1997 | Martin | A61B 17/025 606/105 |
| 5,797,910 | A | * | 8/1998 | Martin | A61B 17/025 606/54 |
| 6,162,223 | A | * | 12/2000 | Orsak | A61B 17/6425 606/59 |
| 6,730,087 | B1 | * | 5/2004 | Butsch | A61B 17/7216 606/105 |
| 6,796,984 | B2 | * | 9/2004 | Soubeiran | A61B 17/7216 606/246 |
| 2002/0151978 | A1 | * | 10/2002 | Zacouto | A61B 17/68 623/17.12 |
| 2003/0204190 | A1 | * | 10/2003 | Li | A61B 17/8004 606/90 |
| 2005/0010233 | A1 | * | 1/2005 | Wittenstein | A61B 17/7216 606/90 |
| 2005/0085815 | A1 | * | 4/2005 | Harms | A61B 17/645 606/279 |
| 2005/0154390 | A1 | * | 7/2005 | Biedermann | A61B 17/7035 128/898 |
| 2005/0171543 | A1 | * | 8/2005 | Timm | A61B 17/7007 606/257 |
| 2005/0203509 | A1 | | 9/2005 | Chinnaian et al. | |
| 2006/0036240 | A1 | * | 2/2006 | Colleran | A61B 17/7025 606/86 A |
| 2006/0155279 | A1 | * | 7/2006 | Ogilvie | A61B 17/6491 606/328 |
| 2006/0189984 | A1 | * | 8/2006 | Fallin | A61B 17/7007 606/250 |
| 2007/0010815 | A1 | * | 1/2007 | Molz | A61B 17/60 606/86 A |
| 2007/0161984 | A1 | * | 7/2007 | Cresina | A61B 17/6425 606/54 |
| 2007/0198088 | A1 | * | 8/2007 | Biedermann | A61B 17/7028 623/17.11 |
| 2008/0195095 | A1 | * | 8/2008 | Renard | A61B 17/6491 606/54 |
| 2008/0275563 | A1 | * | 11/2008 | Makower | A61B 17/68 623/20.21 |
| 2011/0144643 | A1 | * | 6/2011 | Lorenz | A61B 17/6416 606/59 |
| 2014/0107656 | A1 | * | 4/2014 | Masson | A61B 17/7077 606/90 |
| 2014/0276817 | A1 | * | 9/2014 | Murray | A61B 17/62 606/56 |
| 2014/0336648 | A1 | * | 11/2014 | Van Aaken | A61B 17/66 606/58 |
| 2015/0257788 | A1 | * | 9/2015 | Jay | A61B 17/62 606/56 |
| 2016/0095625 | A1 | * | 4/2016 | Sanders | A61B 17/60 606/54 |

\* cited by examiner

EXTERNAL FIXATORS

BACKGROUND OF THE INVENTION

The present invention relates to improving resilient external fixators suitable for being mounted to co-operate with two bone portions between which it is desired to exert traction or else distraction, and finding a particularly advantageous application in treating joint fractures by distraction on the principle of ligamentotaxis in which the traction exerted on either side of the fracture reduces the displacement of the fragments and holds them in a position suitable for encouraging remodeling of the joint.

DESCRIPTION OF THE RELATED ART

The Applicant has made an external fixator that forms the subject matter of European patent No 1 898 815 referred to below as EP-XR.

That resilient external fixator between first and second bone portions comprises a helical spring defined along a first axis, a first body, first means for mounting the first body to co-operate with the helical spring, a first pin suitable for being fastened to said first bone portion, the first pin being oblong in shape and defined along a second axis, the helical spring being suitable for turning relative to the first body about the first axis and the first pin passing through said helical spring, means for mounting the first pin to co-operate with the first body so that the second axis forms a non-zero angle with the first axis, a second body comprising a base and a projecting portion secured, by one of its ends, to the base, one of the ends of the helical spring being mounted in co-operation around the projecting portion, and means for connecting the second body with the second bone portion and said helical spring.

SUMMARY OF THE INVENTION

The improvement made to the above-defined fixator consists in the projecting portion presenting a cross-section that increases in relatively continuous manner from its free end until it reaches its end that is secured to the base, said one of the ends of the helical spring having an inside cross-section that is greater than the cross-section of the free end of the projecting portion and less than the cross-section of the end of the projecting portion that is secured to the base.

BRIEF DESCRIPTION OF THE DRAWING FIGURES

Figure 2:
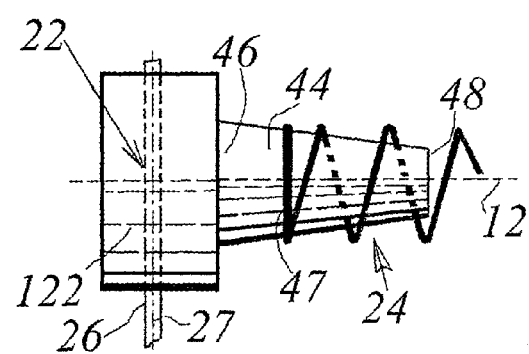

Other characteristics and advantages of the invention appear from the following description given with reference to the accompanying drawings by way of non-limiting illustration, and in which:

FIG. 1 is a diagrammatic side view showing an embodiment of the resilient external fixator as defined in document EP-XR; and FIG. 2 shows, in a diagram taken in combination with the diagram of FIG. 1, an embodiment of a portion of the resilient external fixator of the invention.

DETAILED DESCRIPTION OF THE INVENTION

Firstly, it is stated that in the present description, if the adverb "substantially" is associated with a qualifier of a given means, that qualifier may be understood either in a strict sense or in an approximate sense.

With reference to FIG. 1, the invention described below relates to a resilient external fixator suitable for exerting a resilient force of adjustable intensity between first and second bone portions $O_1$ and $O_2$, and it finds a particularly advantageous application as an external fixator for exerting traction or distraction, both of which can be modulated, between two bones or two bone fractions of a finger, e.g. between two phalanges.

In the embodiment shown in FIG. 1, the external fixator essentially comprises: a helical spring 11 defined along a first axis 12; a first body 14; first means 15 for mounting said first body 14 to co-operate with the helical spring 11 so that the helical spring is capable of pivoting relative to the first body substantially about the first axis 12; a first pin 16 suitable for being fastened to the first bone portion $O_1$, said first pin 16 being oblong in shape along a second axis 17; and means for mounting the first pin 16 to co-operate with the first body 14 so that it passes through the helical spring 11 and so that the second axis 17 forms a non-zero angle with the first axis 12.

In an advantageous embodiment, the pin 16 is a bone pin that is well known in itself, of circularly cylindrical or similar shape, and having an end 46 for penetrating into a bone, which end may include a bone thread, e.g. of the self-tapping type.

By way of example, the means 19 for mounting the first pin 16 to co-operate with the first body 14 are constituted by a through orifice made in the body 14 and of cross-section complementary to that of the pin 16, and advantageously by means for locking the pin in the through orifice and thus relative to the first body 14, such as a fastener screw or the like.

The external fixator of the invention also includes a second body 22 and means 24 for connecting the second body 22 with the second bone portion $O_2$ and with the helical spring 11.

In the embodiment shown in FIG. 1, the means 24 for connecting the second body 22 with the second bone portion $O_2$ and the helical spring 11 comprise: second means 25 for mounting the second body 22 to co-operate with the helical spring 11 so as to allow the spring to pivot relative to the second body about the first axis 12; a second pin 26 suitable for being fastened to the second bone portion $O_2$ and defined along a third axis 27; and means 29 for mounting the second pin 26 to co-operate with the second body 22 so as to pass through the helical spring 11 and so that the third axis 27 forms a non-zero angle relative to the first axis 12.

In an advantageous embodiment, the helical spring 11 has non-touching turns and it is made of a material such as stainless steel, or the like.

By way of example, the second body 22 comprises, as shown in FIG. 4 of document EP-XR, a base 122 and a projecting portion 44 secured, by one 46 of its ends, to the base 122, an end 47 of the helical spring 11 being mounted in co-operation around the projecting portion 44.

The improvement made to the above-defined fixator consists in the projecting portion 44 presenting a cross-section that increases in relatively continuous manner from its free end 48 until it reaches its end 46 that is secured to the base 122, the helical spring having an inside cross-section that is greater than the cross-section of the free end 48 of the projecting portion and less than the cross-section of the end 46 of the projecting portion that is secured to the base 122.

In another characteristic of the invention, the projecting portion 44 is conical in shape, and is preferably in the shape of a circular cone.

The improved resilient external fixator of the invention presents an advantage other than those of the fixator of the prior document referenced above.

As a result of the circularly cylindrical shape of the projecting portion 44 of the prior art fixator, the spring 11 could, for various reasons (vibration, friction, etc.), turn about its longitudinal axis, resulting in an involuntary modification of the strength of the force applied between the two bone portions $O_1$, $O_2$.

In contrast, as a result of the conical shape of the projecting portion 44 of the fixator of the invention, and after adjustment of the spring 11, its end 47 becomes jammed on the conical surface of said projecting portion, this jamming possibly also being accentuated by the practitioner while adjusting the fixator by causing the spring to turn a little about its longitudinal axis, the last turn of the end 47 of the spring thus expanding elastically and increasing friction against the projecting portion.

The invention claimed is:

1. A resilient external fixator between first and second bone portions (O1, O2), comprising:
    a helical spring (11) defined along a first axis (12);
    a first body (14);
    first means (15) for mounting said first body (14) to co-operate with said helical spring (11);
    a first pin (16) suitable for being fastened to said first bone portion (O1), said first pin (16) being oblong in shape and defined along a second axis (17), said helical spring being suitable for turning relative to the first body about the first axis (12) and the first pin (16) passes through said helical spring (11);
    means (19) for mounting said first pin (16) to co-operate with said first body (14) so that said second axis (17) forms a non-zero angle with the first axis (12);
    a second body (22) comprising a base (122) and a projecting portion (44) having a first, free end (48) and a second (46), the base (122) being secured to the second end (46), one (47) of the ends of the helical spring (11) being mounted in co-operation around said projecting portion (44) with the first, free end (48) being located inside the one (47) end of the helical spring (11); and
    means (24) for connecting said second body (22) with said second bone portion (O2) and said helical spring (11), wherein,
    said projecting portion (44) presents an outermost cross-section that continuously increases from the first, free end (48) to the second end (46) that is secured to said base (122), said one (47) end of the helical spring having an inside cross-section that is greater than the outermost cross-section of the first, free end (48) of said projecting portion and less than the outermost cross-section of the second end (46) of said projecting portion that is secured to said base (122), said projecting portion (44) having a first outermost cross-section diameter at the first, free end (48) and a second outermost cross-section diameter at the second end (46) that is secured to said base (122), the first cross-section diameter being less than the second cross-section diameter.

2. A fixator according to claim 1, wherein the projecting portion from the first, free end to the second end has an overall conical shape that continuously increases from the first, free end to the second end.

3. A fixator according to claim 2, wherein the projecting portion from the first, free end to the second end is in the shape of a circular cone that continuously increases from the first, free end to the second end.

4. A fixator according to claim 3, wherein an exterior surface of the portion (44) of the first, free end (48) of the projecting portion located inside the one (47) end of the helical spring (11) is spaced apart from and free of contact with the one (47) end of the helical spring (11).

5. A fixator according to claim 2, wherein an exterior surface of the portion (44) of the first, free end (48) of the projecting portion located inside the one (47) end of the helical spring (11) is spaced apart from and free of contact with the one (47) end of the helical spring (11).

6. A fixator according to claim 1, wherein an exterior surface of the portion (44) of the first, free end (48) of the projecting portion located inside the one (47) end of the helical spring (11) is spaced apart from and free of contact with the one (47) end of the helical spring (11).

7. A resilient external fixator between first and second bone portions (O1, O2), comprising:
    a helical spring (11) defined along a first axis (12);
    a first body (14), said first body (14) being mounted to co-operate with said helical spring (11);
    a first pin (16) suitable for being fastened to said first bone portion (O1), said first pin (16) being oblong in shape and defined along a second axis (17), said helical spring being suitable for turning relative to the first body about the first axis (12) and the first pin (16) passes through said helical spring (11);
    said first pin (16) being mounted to co-operate with said first body (14) so that said second axis (17) forms a non-zero angle with the first axis (12); and
    a second body (22) comprising a base (122) and a projecting portion (44) having a first, free end (48) and a second (46), the base (122) being secured to the second end (46), one (47) of the ends of the helical spring (11) being mounted in co-operation around said projecting portion (44) with the first, free end (48) being located inside the one (47) end of the helical spring (11), said second body (22) being connectable with said second bone portion (O2) and said helical spring (11), wherein,
    said projecting portion (44) has an outermost cross-section surface that increases from the first, free end (48) to the second end (46) that is secured to said base (122), said projecting portion (44) having a first outermost cross-section diameter at the first, free end (48) and a second outermost cross-section diameter at the second end (46) that is secured to said base (122), the first cross-section diameter being less than the second cross-section diameter, and
    said one (47) end of the helical spring has an inside cross-section diameter that is greater than the first outermost cross-section diameter of the first, free end (48) of said projecting portion and less than the second outermost cross-section diameter of the second end (46) of said projecting portion that is secured to said base (122).

8. A fixator according to claim 7, wherein the projecting portion has an overall conical shape that increases from the first, free end to the second end.

9. A fixator according to claim 8, wherein the projecting portion has a circular cone shape that increases from the first, free end to the second end.

10. A fixator according to claim 9, wherein an exterior surface of the portion (44) of the first, free end (48) of the projecting portion located inside the one (47) end of the helical spring (11) is spaced apart from and free of contact with the one (47) end of the helical spring (11).

11. A fixator according to claim 8, wherein an exterior surface of the portion (44) of the first, free end (48) of the projecting portion located inside the one (47) end of the helical spring (11) is spaced apart from and free of contact with the one (47) end of the helical spring (11).

12. A fixator according to claim 7, wherein the projecting portion has an overall conical shape that continuously increases from the first, free end to the second end.

13. A fixator according to claim 12, wherein the projecting portion has a circular cone shape that continuously increases from the first, free end to the second end.

14. A fixator according to claim 7, wherein an exterior surface of the portion (44) of the first, free end (48) of the projecting portion located inside the one (47) end of the helical spring (11) is spaced apart from and free of contact with the one (47) end of the helical spring (11).

\* \* \* \* \*